United States Patent
Galford et al.

(10) Patent No.: US 7,176,682 B2
(45) Date of Patent: Feb. 13, 2007

(54) METHOD AND APPARATUS FOR DETECTING HYDROCARBONS WITH NMR LOGS IN WELLS DRILLED WITH OIL-BASED MUDS

(75) Inventors: James E. Galford, Missouri City, TX (US); Ronald J. M. Bonnie, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 11/029,811

(22) Filed: Jan. 4, 2005

(65) Prior Publication Data

US 2005/0272158 A1 Dec. 8, 2005

Related U.S. Application Data

(60) Provisional application No. 60/534,322, filed on Jan. 4, 2004.

(51) Int. Cl.
*G01V 3/00* (2006.01)

(52) U.S. Cl. .................... 324/303; 324/300

(58) Field of Classification Search ............ 324/303, 324/300, 301, 302, 307, 309, 314
See application file for complete search history.

(56) References Cited

U.S. PATENT DOCUMENTS

| | | | |
|---|---|---|---|
| 5,536,938 A | | 7/1996 | Mills et al. |
| 5,696,448 A | | 12/1997 | Coates et al. |
| 6,107,796 A | * | 8/2000 | Prammer ............... 324/303 |
| 6,737,864 B2 | * | 5/2004 | Prammer et al. ........ 324/303 |
| 6,833,699 B2 | * | 12/2004 | Galford et al. ........ 324/303 |
| 6,838,875 B2 | * | 1/2005 | Freedman ............. 324/303 |
| 6,859,032 B2 | * | 2/2005 | Heaton et al. ........ 324/303 |

OTHER PUBLICATIONS

International Search Report PCT/US05/00162 dated Nov. 9, 2005.

* cited by examiner

*Primary Examiner*—Brij B. Shrivastav
(74) *Attorney, Agent, or Firm*—Jones Day

(57) ABSTRACT

A method and system for estimating native hydrocarbons from oil-based drilling muds with the aid of NMR data. Adaptive echo stacking may be used to balance between precision and sensitivity to changes in the fluid composition. Apparent $T_2$ decay time and effective diffusion constants derived from the NMR data may be transformed into an indication of native hydrocarbon type, using known diffusion constants, fuzzy logic, and neural networks.

20 Claims, 7 Drawing Sheets

METHOD AND APPARATUS FOR DETECTING HYDROCARBONS WITH NMR LOGS IN WELLS DRILLED WITH OIL-BASED MUDS

CROSS REFERENCE TO RELATED APPLICATIONS

This application claims priority of provisional application Ser. No. 60/534,322 filed on Jan. 4, 2004, which is incorporated herein for all purposes.

FIELD OF THE INVENTION

The present invention concerns nuclear magnetic resonance (NMR) logging and more specifically relates to a method and apparatus to identify hydrocarbon bearing intervals and determine gas zones having normal pressure or depleted pressure based on NMR logs, particularly in wells drilled with oil-based muds.

BACKGROUND OF THE INVENTION

In oil and gas exploration it is desirable to understand the structure and properties of the geological formation surrounding a borehole, in order to determine if the formation contains hydrocarbon resources (oil and/or gas), to estimate the amount and producibility of hydrocarbon contained in the formation, and to evaluate the best options for completing the well in production. As discussed below, distinguishing NMR signals due to water in the muds and formation from the NMR signals from native hydrocarbons is known. However, for many reasons, such as for better mechanics of drilling, i.e., well-bore stability, suppression of swelling clays, etc., it is desirable to use oil-based muds instead of water-based muds. This naturally makes the interpretation of NMR signals challenging in the course of evaluating a formation.

The hydrocarbon identification methods used most often with NMR logs, e.g., Time Domain Analysis (TDA), Enhanced Diffusion Method (EDM) etc., rely upon extracting a signal(s) from NMR measurements that is directly related to the amount of hydrocarbon entities present in the tools' sensitive volume. These prior art methods work well in situations where the reservoir is drilled with a water-based mud because the native hydrocarbons have individual NMR properties distinguishable form the properties of the mud. However, when oil-based muds are used, some miscibility is bound to occur between invading oil-based mud filtrate and native hydrocarbons. The miscible solution of oil-based mud filtrate and native hydrocarbon(s) will have NMR relaxation and diffusivity properties which are a combination of NMR fluid properties of the individual hydrocarbon components. Thus, errors can arise when the prior art quantitative methods are applied in situations where oil-based muds are used because the NMR properties of the individual components are not readily distinguishable.

In recent years NMR logging has become very important for purposes of formation evaluation and is one of the preferred methods for determining formation parameters. Improvements in the NMR logging tools, as well as advances in data analysis and interpretation allow log analysts to generate detailed reservoir description reports, including clay-bound and capillary-bound related porosity, estimates of the amounts of bound and free fluids, fluid types (i.e., oil, gas and water), permeability and other properties of interest.

The importance of Nuclear magnetic resonance (NMR) logging, at least in part, is due to the fact that unlike nuclear porosity logs, the NMR measurement is environmentally safe and is unaffected by variations in matrix mineralogy. The NMR logging method is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-laftice relaxation time.

Another related and frequently used NMR logging parameter is the so called spin-spin relaxation time constant $T_2$ (also known as transverse relaxation time) which is an expression of the relaxation due to non-homogeneities in the local magnetic field over the sensing volume of the logging tool.

NMR tools used in practical applications include, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28,1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200; 5,696,448 and 5,936,405. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezigner and Griffin, J. Magn. Reson. 97, 466–485, 1992; and "An Improved NMR Tool Design for Faster Logging," D. McKeon et al., SPWLA 40th Annual Logging Symposium, May–June 1999. The content of the above patents is hereby expressly incorporated by reference for all purposes, and all non-patent references are incorporated by reference for background.

U.S. Pat. No. 6,051,973, assigned to the assignee of this application, which is incorporated herein in its entirety for all purposes, discloses a method and system for measuring a saturation-recovery sequence to reduce errors due to the motion of the logging tool. Motion-independence is achieved, for instance, by issuing a broadband saturation pulse that covers a large volume within the sample, followed by a narrow-band read-out sequence such that the narrow-band is within the broadband saturation pulse.

The MRIL® tool is capable of performing a variety of borehole NMR logging measurements. See, for example, the U.S. Pat. No. 6,242,912 B1, assigned to the assignee of the present application, which teaches systems and methods for lithology independent gas detection. U.S. Pat. No. 6,005,389 assigned to the assignee of the present application teaches the use of a rapid-fire CPMG pulse sequence to detect and quantify components having very short relaxation times, such as clay-bound water. The entire content of these patents is incorporated herein by reference.

NMR tools of the type discussed above generally measure the time for hydrogen nuclei present in the earth formation to realign their spin axes, and consequently their bulk magnetization, either with an externally applied magnetic field, or perpendicularly to the magnetic field, after momentary reorientation due to the application of specific radio frequency (RF) pulses. The externally applied magnetic field is typically provided by a magnet disposed in the tool. The spin axes of the hydrogen nuclei in the earth formation are, in the aggregate, caused to be aligned with the externally applied magnetic field. The NMR tool includes an antenna such that a pulse of radio frequency (RF) power conducted through the antenna induces a magnetic field in the earth formation orthogonal to the externally applied magnetic field. The RF pulse has a duration predetermined to generally align the spin axes of the hydrogen nuclei perpendicular both to the orthogonal magnetic field induced by the RF pulse and to the externally applied magnetic field. After the pulse ends, the nuclear magnetic moment of the hydrogen nuclei gradually relaxes, i.e., returns to their alignment with the externally applied magnetic field; at the same time an antenna, electrically connected to a receiver, helps detect and measure voltages induced in the antenna by precessional rotation of the spin axes of the hydrogen nuclei.

An actual NMR measurement involves a plurality of pulses grouped into pulse sequences, most frequently of the type known in the art as Carr-Purcell-Meiboom-Gill (CMPG) pulsed spin echo sequences. As known in the art, each CPMG sequence consists of a 90-degree (i.e., $\pi/2$) pulse followed by a large number of 180-degree (i.e., $\pi$) pulses. The 90-degree pulse rotates the proton spins into the transverse plane and the 180-degree pulses generate a sequence of spin echoes by refocusing the transverse magnetization after each spin echo.

Another concern in NMR data is the signal-to-noise ratio, which may be improved by experiment stacking. In the multi-frequency MRIL® Prime tool the use of multiple NMR measurement frequencies is conceptually equivalent to the simultaneous acquisition of multiple passes with the earlier logging tools. Thus, MRIL® Prime logs could be acquired at faster logging speeds, with the required SNR obtained by stacking multiple signals across the frequency bands. However, in formations with high-signal levels, this approach may result in more stacking being selected than is necessary to provide adequate signal-to-noise ratio.

An important measurement parameter used in NMR well logging is the diffusion constant D. Generally, diffusion refers to the motion of atoms in a gaseous or liquid state due to their thermal energy. The diffusion D constant is dependent on the pore sizes of the formation and offers much promise as a separate permeability indicator. In a uniform magnetic field, diffusion has little effect on the decay rate of the measured NMR echoes. In a gradient magnetic field, however, diffusion causes atoms to move from their original positions to new ones, which moves also cause these atoms to acquire a different phase shifts compared to atoms that did not move, and thus results in an apparently faster rate of relaxation. Therefore, in a gradient magnetic field diffusion is a logging parameter, which can provide independent information about the structure of the geologic formation of interest, the properties of the fluids in it, and their interaction.

In the paper, entitled "NMR Logging of Natural Gas Reservoirs," presented at the 36$^{th}$ Annual SPWLA Symposium, Paris, Jun. 26–29,1995, Akkurt, R. et al. have shown one approach of using the capabilities provided by HALLIBURTON's MRIL® tool for detection of gas. The content of the Akkurt et al. paper is incorporated herein by reference. In this paper, the authors point out that NMR signals from gas protons are detectable, and derive $T_1$ relaxation and diffusion properties of methane-dominated natural gas mixtures at typical reservoir conditions. The magnetic field gradient of the MRIL® is used to separate and to quantify water, oil and gas saturations based solely on NMR data.

The results in the Akkurt paper are based on the HALLIBURTON's MRIL-CE® tool, the output of which is used to obtain $T_2$ spectra. $T_2$ spectra are extracted from the raw CPMG echo trains by breaking the total NMR signal M(t) into N components, called bins, according to the formula:

$$M(t) = \sum_{i=1}^{N} a_i \exp(-t/T_{2i})$$

where $a_i$ is the porosity associated with the i-th bin. Each bin is characterized by a fixed center transverse relaxation time $T_{2i}$. The total NMR porosity is then determined as the sum of the porosities $a_i$ in all bins. The $T_2$ spectrum model is discussed in detail, for example, in Prammer, M. G., "NMR Pore Size Distributions and Permeability at the Well Site," paper SPE 28368, presented at the 69-th Annual Technical Conference and Exhibition, Society of Petroleum Engineers, New Orleans, Sep. 25–28, 1994, the content of which is incorporated herein for all purposes.

On the basis of the $T_2$ spectra, two methods for detecting gas deposits are proposed in the Akkurt paper and will be considered briefly next to provide relevant background information. The first method is entitled "differential spectrum method" (DSM), which is based on the observation that often light oil and natural gas exhibit distinctly separated $T_2$ measurements in the presence of a magnetic field gradient, even though they may have overlapping $T_1$ measurement values. The DSM makes use of these observations and is illustrated by a specific example for a sandstone reservoir containing brine, light oil and gas. According to the Akkurt et al. paper, two separate logging passes are made with different wait times $TR_1$, and $TR_s$, such that the longer time $TR_1 \geq T_{1g}$, and the shorter time satisfies the relationship $T_{1g} \geq TR_s \geq 3T_{1wmax}$.

Due to the large $T_1$ contrast between the brine and the hydrocarbons the water signal disappears when the spectra of the two signals are subtracted. Thus, the differential $T_2$ spectrum contains only hydrocarbon signals. It should be noted that the subtraction of the $T_2$ spectra also eliminates all bound water, making the DSM very useful in shaly sands.

The second method proposed in the Akkurt et al. paper is called "shifted spectrum method" (SSM). Conceptually the method is based on the observation that since the surface relaxation for gas is negligible, the apparent $T_2$ relaxation can be expressed as:

$$\frac{1}{T_2} = \frac{1}{T_{2B}}\left[1 + \frac{(\gamma G \tau)^2 D T_{2B}}{2}\right]$$

where G is the magnetic field gradient, D is the diffusion coefficient, $\tau$ is half the interecho time, $\gamma$ is the gyromagnetic ratio and $T_{2B}$ refers to the bulk relaxation. It is known in the art that for gas, which is a non-wetting phase, $T_1 = T_{1B} \approx T_{2B}$. Therefore, given that the product $D_0 {}^* T_1$ of a gas after substitution in the expression above is an order of magnitude larger than oil and two orders of magnitude larger than brine, it can be seen that the already large $DT_1$ contrast of gas can be enhanced even further by increasing the inter-echo time, $2\tau$, in order to allow the separation of two fluids that overlap in $T_1$. The SSM is based on the above concept and may result in the signal from gas being shifted out of the detectability range, so that the single spectrum peak is due to brine.

Prior art methods used most often with NMR logs, e.g., Time Domain Analysis (TDA), Enhanced Diffusion Method (EDM), etc. rely on extracting signals from NMR measurements that are directly related to the amount of hydrocarbon present in the tool's sensitive volume. These methods work satisfactorily with Water-Based Muds (WBM) since native hydrocarbons retain their distinct properties. However, with the use of Oil-Based Mud (OBM) and Oil-Based Mud Filtrates (OBMF) in drilling, the NMR signals are due to a combination of native hydrocarbon species and OBMF leakage due to the increased likelihood of miscibility with native hydrocarbons.

It is known that diffusion constants of different components of interest behave differently as a function of $T_2$ relaxation times. Oil and hydrocarbons are generally classified on the basis of viscosity, with the low viscosity oils exhibiting a higher diffusion constant than the high viscosity heavier oils. The diffusion constant of oil also tends to be linearly proportional to the $T_2$ relaxation time. For gases and bulk water the diffusion constant is substantially independent of the $T_2$ relaxation time while being dependent on the temperature. In addition, for gases, the diffusion constant is a function of the pressure.

SUMMARY OF THE INVENTION

Accordingly, an object is to overcome deficiencies associated with the prior art, and, in particular, to provide a method and system for detecting native hydrocarbon types in wells drilled with oil-based muds with NMR while using oil-based mud to improve well-bore stability, suppress of swelling clays, and the like. The difficulties of detecting native oils in the presence of base oils used in the oil-based mud are overcome, in part, by recognizing that OBM filtrate and native hydrocarbons are miscible, and when mixed, form a fluid whose NMR properties are different from those of the individual components. Generally, oils have diffusion constants that are markedly different from gas (for instance, methane). Thus, a miscible mixture of native oil and OBM filtrate will have a lower diffusion constant, and also typically a slower $T_2$ relaxation rate than a miscible mixture of OBM filtrate and gas.

These and other objects are accomplished by a novel approach in which a qualitative estimate of the type of hydrocarbons in a formation surrounding a borehole drilled with an oil-based mud is obtained with the aid of NMR signals by a method comprising: (a) providing a mathematical model for a fluid mixture of native hydrocarbons and oil-based mud in the formation; (b) providing NMR signals from one or more locations in the formation; and (c) estimating the type of native hydrocarbons in the one or more locations in the formation based on the provided mathematical model and the provided NMR signals. This method may also comprise detecting the presence of native oil if presence of gas or a mixture of gas and oil-based mud filtrate does not account for substantially all of the NMR signals. In this method the mathematical model may be based on $T_2$ relaxation and effective diffusion D, and the step of estimating comprises generating, may be based on the NMR signals, an apparent $T_2$ decay time and an effective diffusion constant to construct an apparent $T_2$ relaxation v. effective diffusion constant crossplot; and comparing the mathematical model with the constructed crossplot.

There are several base oils on the market used in oil-based muds. Each of these products may have different NMR properties. Some of the base oils have diffusion constants that are lower than those for native dead oils, others are slightly more diffusive than native dead oils. Similar considerations apply to bulk relaxation times for base oils. Although, the choice of the base oil to allow easy distinction from native hydrocarbons is not required for practicing the invention, such a choice may be made at the outset. Even if the selected base oil has NMR properties similar to those of native oils, it is still possible to qualitatively estimate hydrocarbon types. The process of qualitatively identifying the native hydrocarbon types then operates as a process of elimination; in which if detected hydrocarbon deposits are not substantially gaseous in nature, then they are identified as oil.

Thus, when the base oils and native oils are distinct, then the method may include distinguishing, based on the crossplot, native oils from the oil-based mud. Further, the method may comprising selecting a base oil in the oil-based mud to facilitate distinguishing native oils from the oil-based mud. A known diffusion constant for at least one oil used in the oil-based mud may allow estimation of the oil-based mud contributions to the $T_2$ v. diffusion constant crossplot. This method may also comprise the step of distinguishing native oils from the oil-based mud in at least one of said one or more locations in the formation. This method may also comprise selecting at least one oil with known properties in the oil-based mud in the step of providing the mathematical model. In this method step (a) may comprise modeling boundaries between native hydrocarbon types and oil-based mud in the mathematical model. This method may also comprise the step of providing a resistivity log to assist in modeling boundaries between native hydrocarbon types and oil-based mud. In this method the step of modeling boundaries may comprise using one or more of: (1) fuzzy logic rules; (2) neural network modeling; and (3) empirical observations.

In a preferred embodiment, a method for nuclear magnetic resonance (NMR) based estimation of petrophysical properties of an earth formation surrounding a well drilled with oil-based muds, comprises generating one or more of differential NMR signals adjusted to reduce contributions from water; estimating an apparent $T_2$ decay time and an effective diffusion constant from the one or more of the differential NMR signals; and transforming the apparent $T_2$ decay time and effective diffusion constant into an indication of contributions of hydrocarbon types, such as gas mixed with oil-based muds, gas alone, native oils, and native oil mixed with oil-based mud, wherein the step of transforming is performed using one or more of: (1) a known diffusion constant for an oil-based mud; (2) fuzzy logic for assigning NMR signals to one or more by hydrocarbon types; and (3) neural networks for dynamically adjusting the network response to input signals from known hydrocarbon types.

In this method, an array of echo differences may be constructed by taking the difference between a long wait time echo train and a short wait time echo train echo by echo. In this method, the apparent $T_2$ decay time may be estimated using a functional model describing signal decay in the array of echo differences. In this method, the apparent $T_2$ decay time may also be estimated by using a stretched exponential function:

$$E(t) = Ae^{-\left[\frac{t}{T_2}\right]^\alpha},$$

wherein, E(t) represents the differential echo amplitude at echo time, t; A represents an amplitude of a differential signal; and a is the stretch factor.

In this method, the differential NMR signals may be generated by the differential spectrum method. Furthermore, each of the differential NMR signals may be obtained by subtracting a short wait time $T_2$ distribution from a long wait time $T_2$ distribution at corresponding inter-echo times. In this method, the apparent $T_{2B}$ bulk decay time and the effective diffusion constant may be estimated using the expressions:

$$\frac{1}{T_{2S}} = \frac{1}{T_{2B}} + \frac{D(\gamma G c T E_S)^2}{12}, \text{ and, } \frac{1}{T_{2L}} = \frac{1}{T_{2B}} + \frac{D(\gamma G c T E_L)^2}{12},$$

wherein γ represents the gyromagnetic ratio for hydrogen protons, G is the magnetic field gradient, c is a constant for taking into account combined effects of spin dynamics associated with mixing of direct and simulated echoes in a gradient magnetic field, $T_{2S}$ is a decay time for a short interecho time, $T_{2L}$ is a decay time for a long interecho time, $T_{ES}$ is a short inter-echo spacing, and $T_{EL}$ is a long inter-echo spacing.

This method may further comprise the step of resolving ambiguities between mixture of oil-based mud filtrate and native oils and/or condensate on one hand and water bearing formation invaded with oil-based mud by a deep reading resistivity log on the other hand. This method may further comprise confirming detection of a native hydrocarbon with the aid of one or more of a porosity and a resistivity log.

In a preferred embodiment, a method for obtaining an estimate, based on NMR signals, of hydrocarbons in a formation surrounding a borehole drilled with the aid of oil-based mud, comprises: constructing an array of echo differences by taking the echo-by-echo difference between a long wait time and a short wait time echo trains; estimating an apparent $T_2$ decay time in the array of echo differences; and estimating native hydrocarbon contributions to the apparent $T_2$ decay time to obtain an indication of native oil type, based at least in part on a failure of a gas contribution to substantially account for the estimated apparent $T_2$ decay time.

In this method, the indication of the native oil type may be confirmed with the aid of one or more of a porosity and a resitivity log. In this method, the step of estimating native hydrocarbon contributions may comprise constructing an apparent $T_2$ decay time versus effective diffusion constant plot, which distinguishes between native hydrocarbons and the oil-based mud by taking into account a known diffusion constant for an oil used in the oil-based mud.

The contemplated embodiments also include configuring one or more processors to process NMR signals from a formation surrounding a borehole in accordance with the methods described herein.

These and other features and advantages are further explained with the aid of the following illustrative figures.

DETAILED DESCRIPTION OF THE PREFERRED EMBODIMENTS

Figure 1:
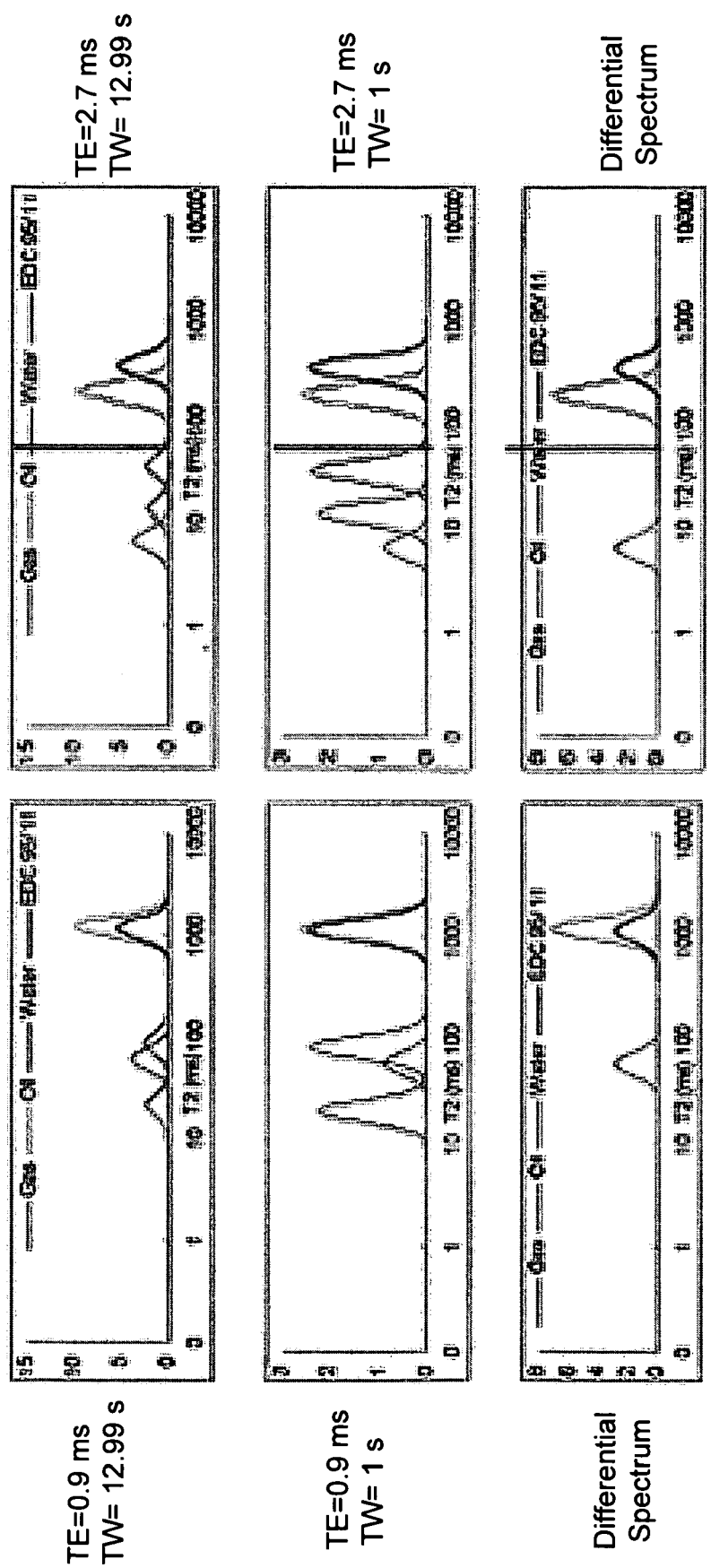
FIG. 1 shows illustrative NMR signals for two wait times and two inter-echo spacings along with derived differential signals.

A system and method are disclosed for identifying native hydrocarbons in wells drilled with oil-based muds by making qualitative assessments of apparent NMR parameters derived from NMR logging measurements. The disclosed new system and method identify the type of native hydrocarbon present in reservoirs drilled with oil-based muds by performing a multi-dimensional qualitative analysis of data from multiple NMR measurements. Inputs from other logging measurements such as conventional nuclear porosity and resistivity logs may also be used to supplement, or confirm the results obtained from the NMR analysis.

The techniques disclosed herein are also applicable in wells drilled with oil-based muds where quantitative evaluations of hydrocarbon volumes are not required, as a simple qualitative discrimination of hydrocarbon type is desired. In addition, the disclosed techniques may be helpful for identifying depleted gas zones.

The disclosed approach accommodates the miscible mixing of oil-based mud filtrate with native hydrocarbons by using a combination of NMR measurements involving different inter-echo spacings and wait times together with inputs from conventional porosity and resitivity logs to obtain a qualitative identification of the type of hydrocarbon present. A basic evaluation of is made first using the NMR techniques to affirm the qualitative detection of native hydrocarbon and discriminate NMR response in water-bearing intervals invaded with oil-based muds.

Dissolved gas causes a displacement from the "dead oil" trend. For low and intermediate viscosity dead oils, the trend is fairly linear between observed $T_2$ and D as shown. However for the MRIL® tool, or any other tools that have a magnetic field gradient, the diffusion relaxation becomes the dominate relaxation mode as viscosity becomes lower and lower. At some point this results in the observed $T_2$ becoming double valued and the dead oil trend actually reaches a maximum as illustrated in FIG. 4. The condensates in FIG. 3 comprise very light oils. The y axis of these plots is the observed $T_2$ relaxation time, not bulk $T_2$ relaxation time. Thus, it includes effects from the diffusion-relaxation mode. In accordance with the inverse relationship between viscosity and bulk diffusion constant, the "condensates" exhibit a lower viscosity than the light and intermediate oils. For instance, if a low or intermediate viscosity oil had dissolved in it a sufficient quantity of gas, the mixture may have diffusion properties resembling a very light oil with no gas dissolved in it.

In order to separate signal contributions from different fluids, an NMR tool must be able to operate in a three-dimensional parameter space: $T_2$ (transverse decay time), measured by a CPMG pulse-echo sequence: $T_1$ (longitudinal polarization time), measured by variable saturation-recovery times; and D (apparent, restricted diffusivity), measured by varying the CPMG pulse-echo spacing τ in the presence of a magnetic field gradient.

In a preferred embodiment, measurements in a moving logging tool are enabled using, in relatively general form, apparatus for carrying out NMR borehole diffusion coefficient determinations. The apparatus includes a first portion, which is arranged to be lowered into a borehole in order to examine the nature of materials in the vicinity of the borehole.

The first portion comprises a magnet or a plurality of magnets, which generate a substantially uniform static magnetic field in a volume of investigation. The first portion also comprises an RF antenna coil, which produces an RF magnetic field at the volume of investigation which field is substantially perpendicular to the static magnetic field.

In addition to the static magnetic field gradient generated by magnet(s), an optional magnetic field gradient coil, or plurality of coils, can also be used to generate a magnetic field gradient at the volume of investigation. This additional contribution to the magnetic field has a field direction preferably collinear with the substantially uniform field and has a substantially uniform magnetic field gradient, which may or may not be switched on and off by switching the dc current flowing through the coil or coils.

The antenna together with a transmitter/receiver (T/R) matching circuit typically include a resonance capacitor, a T/R switch and both to-transmitter and to-receiver matching circuitry and are coupled to an RF power amplifier and a receiver preamplifier. A power supply provides the dc current required for the magnetic field gradient generating coils. All the elements described above are normally contained in a housing, which is passed through the borehole. Alternatively, some of the above elements may be located above ground.

The control circuitry for the logging apparatus may include a computer, which provides a control output to a pulse programmer, which receives an RF input from a variable frequency RF source. The Pulse programmer controls the operation of the variable frequency RF source as well as an RF driver, which receives an input from the variable frequency RF source and outputs to an RF power amplifier.

The complex time-domain signal from the RF receiver preamplifier is supplied to an RF receiver, which optionally receives input from a phase shifter. Phase correction may be performed using signal-processing algorithms. Pulse programmer controls the gradient coil power supply enabling and disabling the flow of current, and hence controls the generation of static or pulsed field gradients, according to the commands of the computer. Some or all of the elements described above may be disposed in an above ground housing and/or below ground. Improved devices and measurement methods, which can be used with or as the probe, are described generally in U.S. Pat. Nos. 4,710,713; 4,717,876; 4,717,877; 4,717,878, 5,212,447; 5,280,243; 5,309,098 and 5,412,320 all of which are commonly owned by the assignee of the present application. A useful specific embodiment of the tool is also discussed in detail in Chandler et al., "Improved Log Quality with a Dual-Frequency Pulsed NMR Tool," paper SPE 28365, presented at the 69-th Annual Technical Conference and Exhibition, Society of Petroleum Engineers, New Orleans, Sep. 25–28, 1994. The contents of these patents and the Chandler et al. paper are hereby expressly incorporated for all purposes.

The MRIL® tool, used in a preferred embodiment, is digitally based, so that raw echo data is digitized at the carrier frequency and all subsequent filtering and detection is performed in the digital domain. The system is typically capable of "hopping" from one operating frequency to another, the effect of which includes shifting the radial position of the resonant volume for the tool. The frequency shift is selected in such manner that at least two non-overlapping resonant volumes are formed; each new resonant volume associated with a different frequency being filled with fully relaxed protons. Hopping between two or more (i.e., K) frequencies thus allows reducing the time between experiments approximately by a factor of K, without compromising complete $T_1$ measurements or adopting imprecise empirical $T_1/T_2$ relationships; the logging speed for the tool can accordingly be increased approximately K times. Preferably, each frequency band is about 6 kHz wide and the two mean band frequencies are offset by about 15 kHz. This mode of operation forms two concentric annuli, each 0.04 inch (0.1 cm) thick, separated center to center by about 0.09 inches (0.23 cm).

The logging speed of the device used in a preferred embodiment depends upon different factors including the SNR of the received signal, the desired log precision and vertical resolution, and the cycle time permitted by the $T_1$, parameter of the formation. Preferably, for greater than 95% recovery within a single resonant volume, the recovery time typically should satisfy $T_R \geq 3T_1$. As a consequence of the multi-frequency operation, the cycle time is only slightly longer than the $T_R$ normalized to the number of frequencies employed. (i.e. $T_C \approx T_R/2$ for two operating frequencies).

The MRIL® tool has a vertical excitation/response function that can be represented by a near-perfect rectangular aperture. In a preferred embodiment, a high vertical resolution, 24" (60.96 cm) long aperture, or a lower vertical resolution, 43" (109.22 cm) long, aperture are used.

The CPMG pulse sequences used with the MRIL® tool in a preferred embodiment have been described generally in U.S. Pat. No. 5,212,447 assigned to the assignee of the present application. Also discussed in this patent are specific methods of conducting NMR measurements, including derivations of the diffusion coefficient D and/or $T_2$. U.S. Pat. No. 5,212,447 is incorporated herein by reference.

A MRIL® tool used in a preferred embodiment may store multiple pulse sequences downhole, in a memory within the probe. These sequences are then activated by commands from the measurement time controller of the surface system. At the surface, raw tool data are separated into data streams and associated with the correct calibration and correction tables in data processor. An essentially unlimited number of pulse sequences can be used quasi-simultaneously, as described in more detail next. In an alternative preferred embodiment, the operation of the tool can be re-programmed on command from surface controller.

The signal processing is directed to the detection of hydrocarbons (oil and gas), which are assumed to be the non-wetting phase, i.e., to be generally characterized by their bulk relaxation properties. The effects of temperature and pressure on $T_1$ and D of the gas phase substantially cancel each other, resulting in fairly stable and predictable values for both parameters, for which mathematical expressions are available. On the other hand, the corresponding values for the oil phase are generally dependent on the formation.

The hydrogen index (HI) of oil is often assumed to be 1.0. The measured drop in NMR porosity is typically observed in gas zones, predominantly methane, because $HI_g<1$. In overpressured reservoirs $HI_g$ can be about 0.7. Accordingly, the gas HI is sufficient to give readily detectable signals from gas. In an alternative preferred embodiment, the hydrogen index of different hydrocarbons can also be estimated using the expressions presented, for example, in "Schlumberger: Log Interpretation Principles/Applications," Schlumberger Educational Services, 1989, pp. 5–20 and 5–21, the content of which is expressly incorporated herein.

The apparent diffusivity D of a fluid depends both on the self-diffusion coefficient $D_0$ and the restrictions imposed by the pore space. Because of diffusion, the intrinsic relaxation rate $1/T_{2,g}$ for gas is negligible compared to $1/T_{2,g}^†$. Similarly, the diffusivity of the oil phase is small compared to that of the gas phase. Consequently, the parameters $T_{2,o}$ and $T_{2,o}^†t$ are much larger than both $T_{2,g}^†$ and also much larger than the total acquisition time required to separate oil from gas signals. The self-diffusion coefficients $D_0$ for methane is at least about 50 times larger than that of water and light oil. The resulting contrasts in the measured $T_2$ (i.e., $T_{2r}$) for gas compared to oil is useful in distinguishing between native gas deposits and oils.

Further details of the construction and operation of the tool used in a preferred embodiment can be found in U.S. Pat. Nos. 4,710,713 4,717,876; 4,717,877; 4,717,878; 5,212,447; 5,280,243; 5,309,098; 5,412,320; 5,517,115, 5,557,200 and 5,696,448. The content of the above patents is hereby expressly incorporated by reference. It will be appreciated that while the MRIL® tool is used in a preferred embodiment, any other tool notably the CMR and CMR-Plus tools by Schlumberger, or other available tools, such as those by Baker-Atlas and Computalog, as well as logging-while-drilling (LWD) tools, appropriately programmed, can also be used in alternative embodiments.

In one aspect, differentiating native hydrocarbons from OBM components is done using different NMR-based properties that various fluid mixtures exhibit. For example, in a specific embodiment, one can use a cross-plot illustrating the properties of a fluid mixture in terms of two or more distinct fluid properties. In a preferred embodiment, illustrated herein, a cross-plot is provided using the $T_2$ relaxation and diffusion Ø properties.

In accordance with this embodiment, there are several ways to use values of observed $T_2$ and D and to determine the type of the detected hydrocarbons. In particular, identifying the hydrocarbon types may be treated as a pattern recognition problem. For instance, recognizing the hydrocarbon type may rely on "mapping" the $T_2$-D crossplot into regions associated with oils (OBM-oil mixtures) and OBM-gas mixtures, and perhaps OBM-low pressure gas mixtures, such as those shown in FIGS. 3, 4, and 7. The identification of the detected fluid mixture is preferably based on the region of the cross-plot in which a data point falls. Determination of the boundaries for the different regions of the plot can be done in several different ways, including empirical observations, mathematical modeling, or some combination of modeling with apriori knowledge. In a specific embodiment, this determination of the boundaries is done using fuzzy logic, which takes into account the possibility that the boundaries of the regions may not be precisely known, or that points in the neighborhood of the boundaries may identify the hydrocarbon as one type or other. In other words, near the boundaries, the estimate may sometimes be gray and thus be assigned a probability value instead of a "black or white" determination of whether the measured fluid mixture is inside or outside a region. Thus, in a preferred embodiment, a given set of rules is applied for establishing the boundaries of different regions and the cross-plot. The specific rules applied are not critical to the application of the principles of this invention. However, it is important to recognize that the boundaries of the various regions are not fixed; and may change with logging conditions of temperature and pressure, the type of MRIL® tool used, and the type of OBM used.

The detectable NMR response to a miscible mixture of oil-based mud and native hydrocarbons may be visualized in the context of the standalone NMR differential spectrum method (DSM) for hydrocarbon typing with the aid of FIG. 1. As seen for the two sets of panels in FIG. 1, differential signals for individual hydrocarbon entities (for instance, methane, light oil, and oil-based mud filtrate) may be anticipated at predictable decay times for a given set of circumstances (such as formation temperature and pressure and native oil viscosity) and wait times for various combinations of inter-echo spacings.

In the DSM methodology, used in one embodiment, the differential signal is obtained by subtracting a short wait time $T_2$ signal distribution from a long wait time $T_2$ signal distribution at the corresponding inter-echo time. The differential signal can frequently be manipulated to include only signals from hydrocarbons by choosing a short wait time that sufficiently captures the entire water signal, so that the water signal is cancelled in the subtraction operation. These individual decay signals can be thought of as being end points for binary mixtures of oil-based mud filtrate with gas or native oil.

Accordingly, the decay time for a given mixture is expected to occur at a decay time that is some function of the relative volumes of individual end point components. For gradient magnetic field NMR logging instruments such as the MRIL® tool, the influences of self induced diffusion result in the decay time end points occurring at smaller decay time with increasing inter-echo spacing as shown in the right hand set of panels in FIG. 1. The relative shift in the decay times for the end points among the differential spectra in going from one inter-echo spacing to another depends on the relative NMR diffusivity of the individual fluids.

Figure 2:
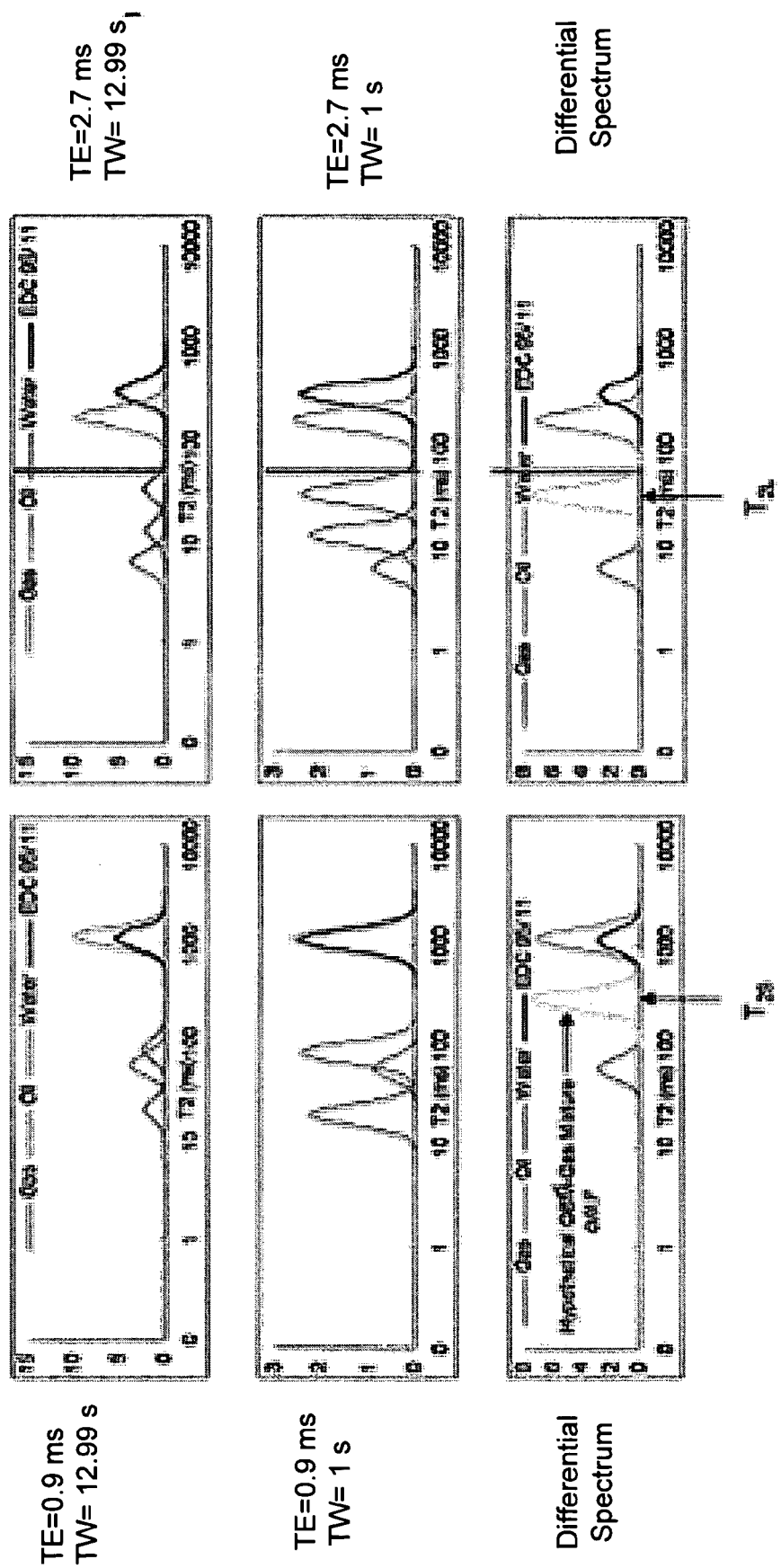
FIG. 2 shows illustrative NMR signal similar to those in FIG. 1 along with differential signal resulting from a hypothetical binary, oil-based mud filtrate (OBMF)-gas mixture for each inter-echo spacing.

The lower panels in FIG. 2 show a differential signal resulting from a hypothetical binary, oil-based mud filtrate (OBMF)—gas mixture for each inter-echo spacing, which correspond to observed decays times, $T_{2S}$, for the short inter-echo spacing and $T_{2L}$, for the long inter-echo spacing. Each of these observed decay times can be expressed in terms of bulk relaxation time, $T_{2B}$, and effective diffusion constant, D, as:

$$\frac{1}{T_{2S}} = \frac{1}{T_{2B}} + \frac{D(\gamma G c TE_S)^2}{12}, \text{ and } \frac{1}{T_{2L}} = \frac{1}{T_{2B}} + \frac{D(\gamma G c TE_L)^2}{12},$$

wherein γ represents a gyromagnetic ratio for hydrogen protons, G is the magnetic field gradient, c is a constant for taking into account combined effects of spin dynamics associated with mixing of direct and simulated echoes in a gradient magnetic field, $T_{2S}$ is a decay time for a short interecho time, $T_{2L}$ is a decay time for a long interecho time, $TE_S$ is a short inter-echo spacing, and $TE_L$ is a long inter-echo spacing. Although illustrated with two inter-echo spacings, this approach can be extended to data sets consisting of more than two different inter-echo spacing measurements.

The observed relaxation time obtained from differential signals for one or more inter-echo times and the derived effective diffusion constant can provide an indication of the hydrocarbon type of the fluid mixture by taking advantage of the substantially larger diffusion constant for most natural gases compared to those of light native oils and oil-based mud filtrates.

Figure 3:
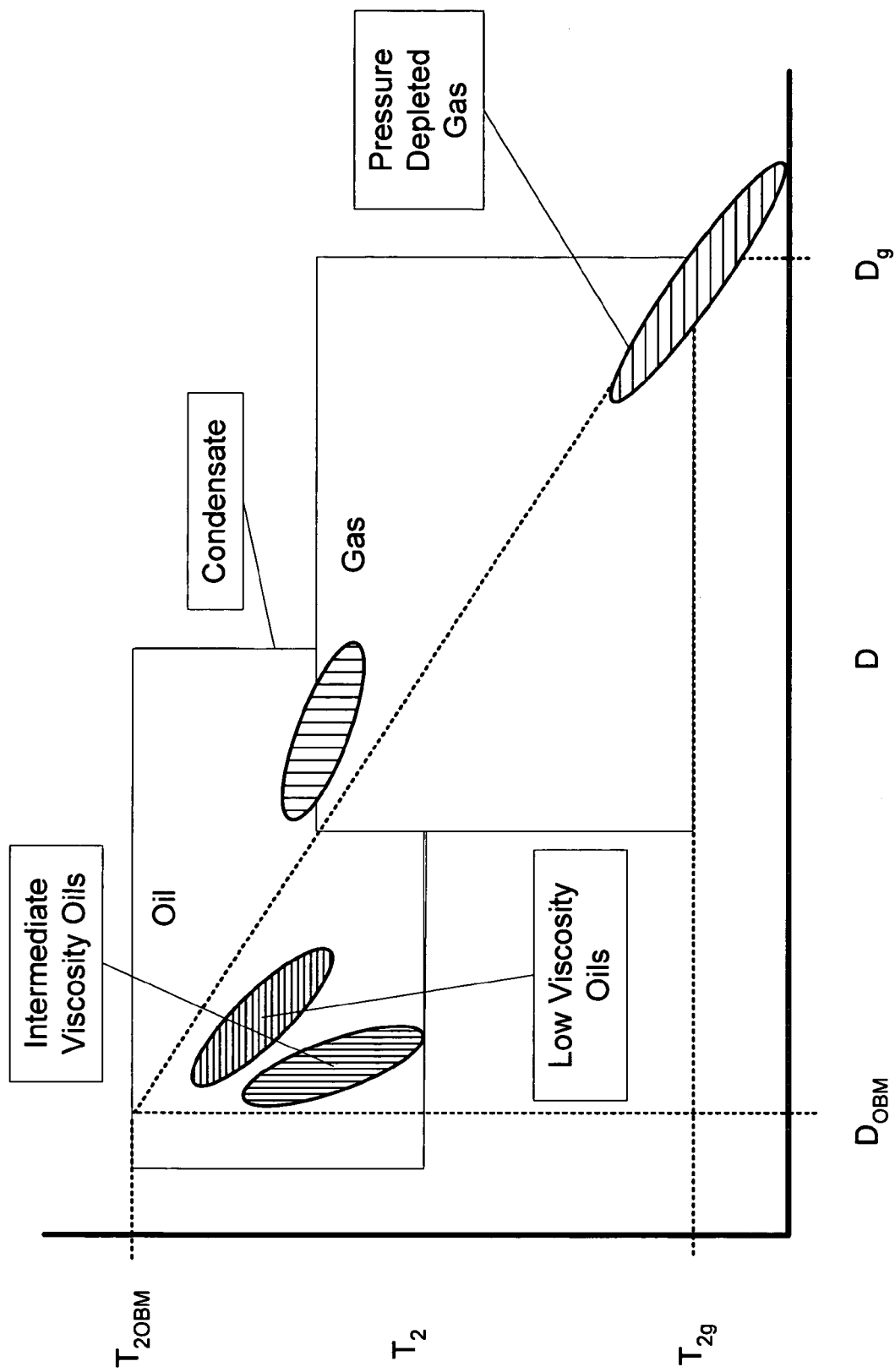
FIG. 3 shows an illustrative mapping of apparent $T_2$ (for the differential signal from one inter-echo spacing) against the effective diffusion constant.
Figure 4:
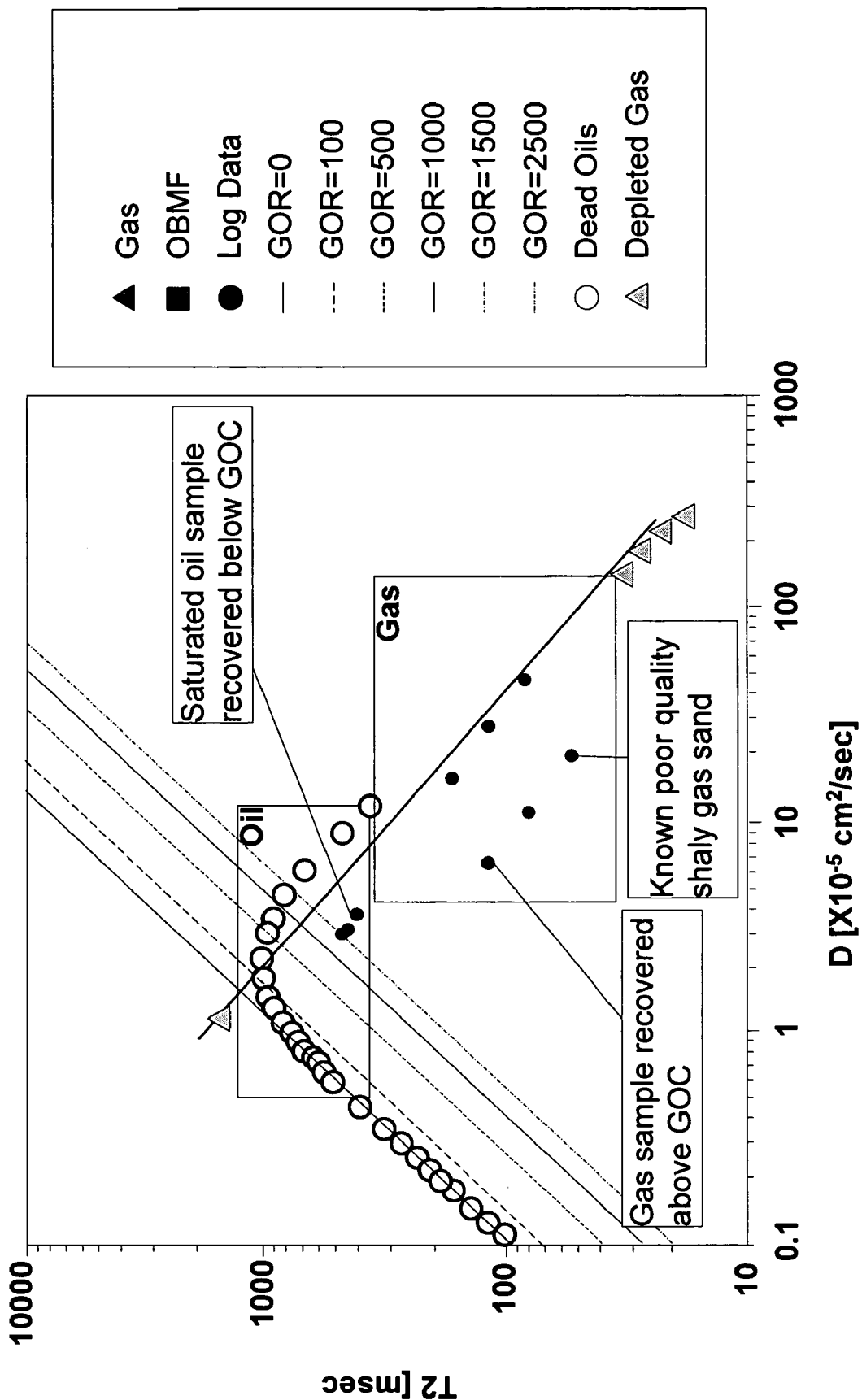
FIG. 4 shows illustrative data from several reservoir intervals in a well drilled with oil-based muds showing the distinct regions in a $T_2$- diffusion constant crossplot that are occupied by native oils, gases, depleted gas zones and base oils and oil-based mud filtrates.

FIG. 3 shows a mapping of apparent $T_2$ for the differential signal from one inter-echo spacing, e.g., $TE_S$, compared to the effective diffusion constant, which could be used in a specific embodiment to qualitatively identify the native hydrocarbon as being gas, low viscosity oil, intermediate viscosity oil, or condensate. This distinction takes advantage of the tendency for light oils, condensates, and base-oil filtrates to cluster in a region characterized by longer apparent decay times and smaller diffusion constants compared to mixtures comprised of methane and oil-based mud filtrate. Notably, a map as shown in FIG. 3 may also be used to detect pressure depleted gas zones. In particular, one of skill in the art would appreciate that points clustering in the vicinity of pure methane ($D_g$, $T_{2g}$) at normal reservoir conditions, and to the southeast, would be consistent with isothermal pressure depletion through production because the bulk diffusion constant for methane is inversely proportional to its density.

It will be appreciated that sometimes the $T_2$-D crossplot shown in FIG. 3 may not be sufficient to distinguish the miscible response caused by a mixture of oil-based mud filtrate and oil or condensate in a hydrocarbon zone from a water bearing formation invaded with oil-based mud filtrate. In a preferred embodiment, such ambiguities may be resolved with the aid of a deep-reading resistivity log. Advantageously, hydrocarbon identification of fluid types from an observed $T_2$ v. apparent D map, as suggested by FIG. 3, often does not require a detailed understanding of the mixing rules for the particular fluids.

In addition, correlation functions exist for predicting the observed $T_2$ and diffusion D constant for many commercial base oils present in oil-based muds and gases, such as methane, as functions of temperature and pressure. By using the existing correlation functions, the observed $T_2$-apparent V.D map can be made to adapt to changing reservoir conditions.

An alternative approach in accordance with a different aspect of the invention does not use differential $T_2$ spectra as described above with the use of dual wait time NMR measurements at different inter-echo spacings to obtain observed decay times from mixtures of oil-based mud filtrate and native hydrocarbons. Instead, in the alternative approach, the apparent $T_2$ decay time for each pair of inter-echo spacing measurements is obtained by using a search algorithm to find the optimum value, which describes the signal decay contained in an array of echo differences. Using this approach, the array of echo differences, for an inter-echo spacing, is constructed by taking the difference between the long wait time and short wait time echo trains echo by echo. A variety of $T_2$ decay time models can be applied to extract the apparent $T_2$ decay time from the resulting echo difference array. A stretched exponential of the form:

$$E(t) = Ae^{-\left[\frac{t}{T_2}\right]^\alpha}$$

is used in a preferred embodiment, where E(t) represents the differential echo amplitude at echo time, t; A represents an amplitude of a differential signal; and a is a stretch factor.

The stretch exponential decay model provides an additional degree of freedom to approximate the complex decay spectra associated with OBMF and native oils. In this embodiment, the alpha parameter is used in fitting the echo difference array to extract a single decay time. The idea is that by fitting a stretched exponential, the solution becomes more stable and less sensitive to noise. It also has the effect of fitting for a "signature," which resembles a Gaussian distribution of decay times about the extracted $T_2$.

In a preferred embodiment, a number of echo difference arrays are stacked to improve the signal to noise ratio of the differential signal and thereby improve the precision of the extracted apparent $T_2$ decay times (and the effective diffusion constant). In order to achieve a compromise among the precision of the extracted differential decay information and the sensitivity to changes in fluid characteristics, an adaptive stacking algorithm is preferred, where the number of echo difference arrays stacked can vary with signal quality. In this context, the echo difference arrays represent a depth-wise sampling of signal content from a continuous log. Thus, the number of stacked echo difference arrays in this context represents several depth samples of recorded information.

Experiment stacking is used to improve the signal-to-noise ratio (SNR) to an adequate level. It should be noted that for multi-frequency tools, such as the MRIL® Prime tool, this means that the experiment stacking may be performed across one or more frequencies depending on how the data was acquired.

Typically, for stacking purposes, filters with no other length constraints are often an improvement over the filters in which the filter length is calculated as a multiple of the number of frequencies and phase alternate pairs (PAPs). Therefore, where the data dictates it, in accordance with a preferred embodiment one can use a boxcar filter of length 10, whereas in prior art stacking one would have to use a filter of length 16, which introduces processing delays and may lead to decreased vertical resolution of the data.

Alternatively, other types of filters can be used advantageously and may be more appropriate for achieving the desired signal-to-noise ratio. For example, adaptive filters allow the stacking to vary to allow a tradeoff between the precision of the extracted decay information and the changes in fluid characteristics.

Any suitable approach for transforming an extracted apparent $T_2$ decay time and effective diffusion constant into a qualitative indication of the native hydrocarbon type is a part of a preferred embodiment. Any number of methods, including a two (or higher)-dimensional map with bounded regions similar to the illustration in FIG. 3, could be applied to achieve this goal. Alternatives, such as fuzzy logic and neural networks, could be applied, especially in conjunction with the influences of hydrocarbons on other logging measurements in a multi-dimensional evaluation to provide a more robust indication of the hydrocarbon type.

EXPERIMENTAL PROOF

FIG. 4 shows data from several reservoir intervals in an OBM drilled Gulf of Mexico well. The responses to pure OBMF are indicated by the square symbols in the upper left of the shaded oil region. Responses to pure methane are indicated at the lower right corner of the shaded gas region with a series of points (triangles) below and to the right of which represent responses to methane at pressures below normal reservoir pressure. The shaded circles show the responses to dead crude oils computed using the customary temperature-viscosity correlations functions; these points represent liquid hydrocarbons for a range of viscosity at reservoir temperature conditions. Data obtained by applying the methods described above for extracting the apparent $T_2$ decay time and effective bulk diffusion constant from echo difference arrays stacked over various reservoir intervals are shown by the black circles.

Figure 5:
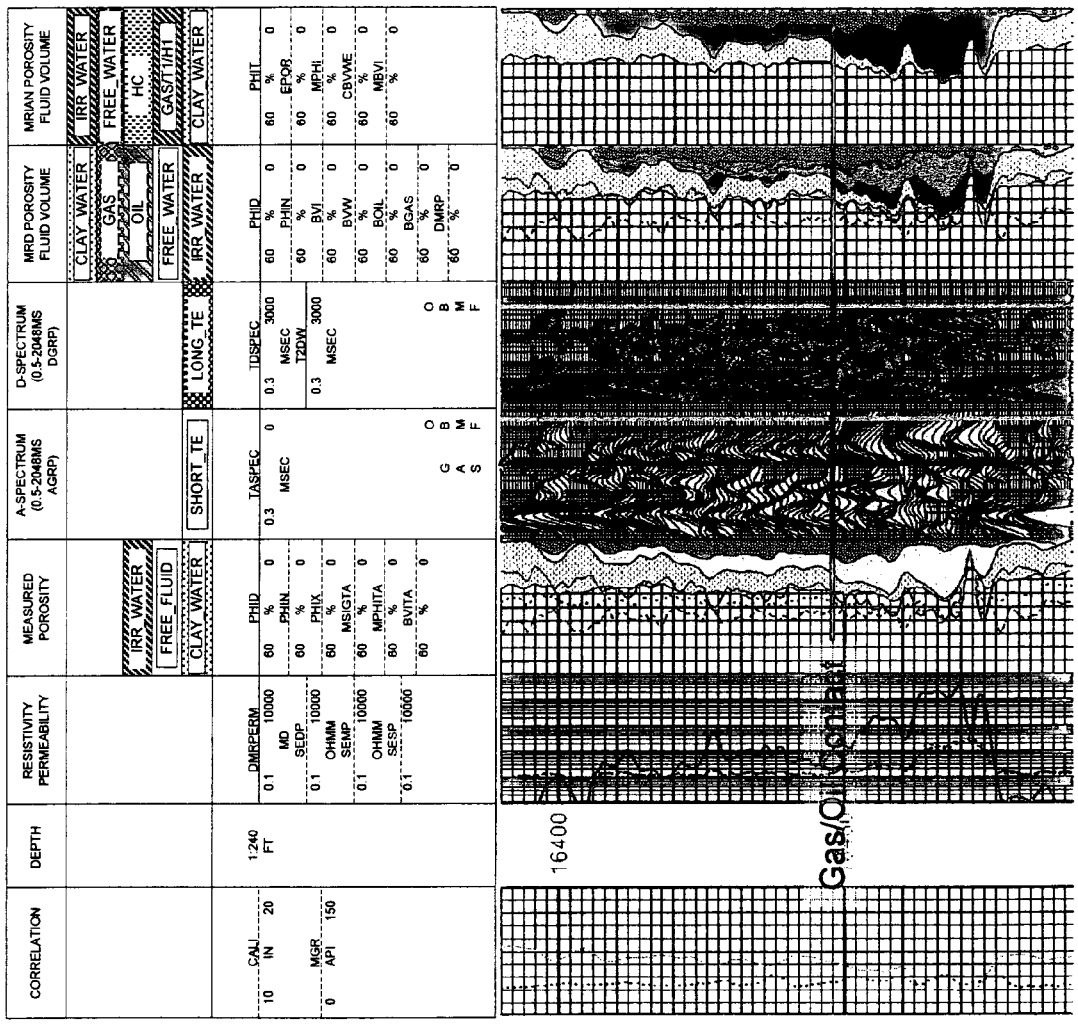
FIG. 5 shows log data from several different kinds of measurements to illustrate the identification of boundaries and zones containing different kinds of formation fluids and gases by consolidating them.

As can be seen from the data, oil zones in this well are readily distinguished from gas bearing intervals. It is interesting to note two of the points shown in FIG. 4 that are from data obtained from the same reservoir, were derived from stacked echo differences above and below the gas-oil contact indicated in FIG. 5. Samples collected with a downhole fluid sampler confirm the identification of these points as indicated in FIG. 4.

The responses in the oil zones tend to fall below and to the right of computed dead oil responses. This response may be interpreted as being caused by a mixture of OBMF and live oil at moderate gas to oil ratio (GOR). Lines of various GOR can be constructed, based on the work done by Lo et al., as shown in FIG. 4 to illustrate the effect of solution gas on low viscosity oils. From this it is easy to see the response to a pure live oil at downhole conditions would lie somewhere to the lower right of the dead oil prediction. Thus, the response of the miscible native live oil and OBMF can also fall to the lower right of the locus of dead oil points depending on the relative mixing of the two fluids.

The points in the gas region of FIG. 4 tend to occur at some distance from the predicted response of methane. This is interpreted to confirm the miscible mixing of formation gas and OBMF. This tendency, which is also noted in a second example shown in FIG. 7, suggests actual points falling in the neighborhood of the pure methane response and to the lower right (predicted depleted gas points) could be interpreted to indicate miscible mixing of pressure depleted gas and OBMF. The three gas points located close to the line joining the OBMF and methane response points in FIG. 4 are from clean high quality sandstone reservoirs with obvious, strong gas cross-over on the conventional neutron and density logs as well as substantial hydrogen index effect on the measured MRIL® porosity.

Figure 6:
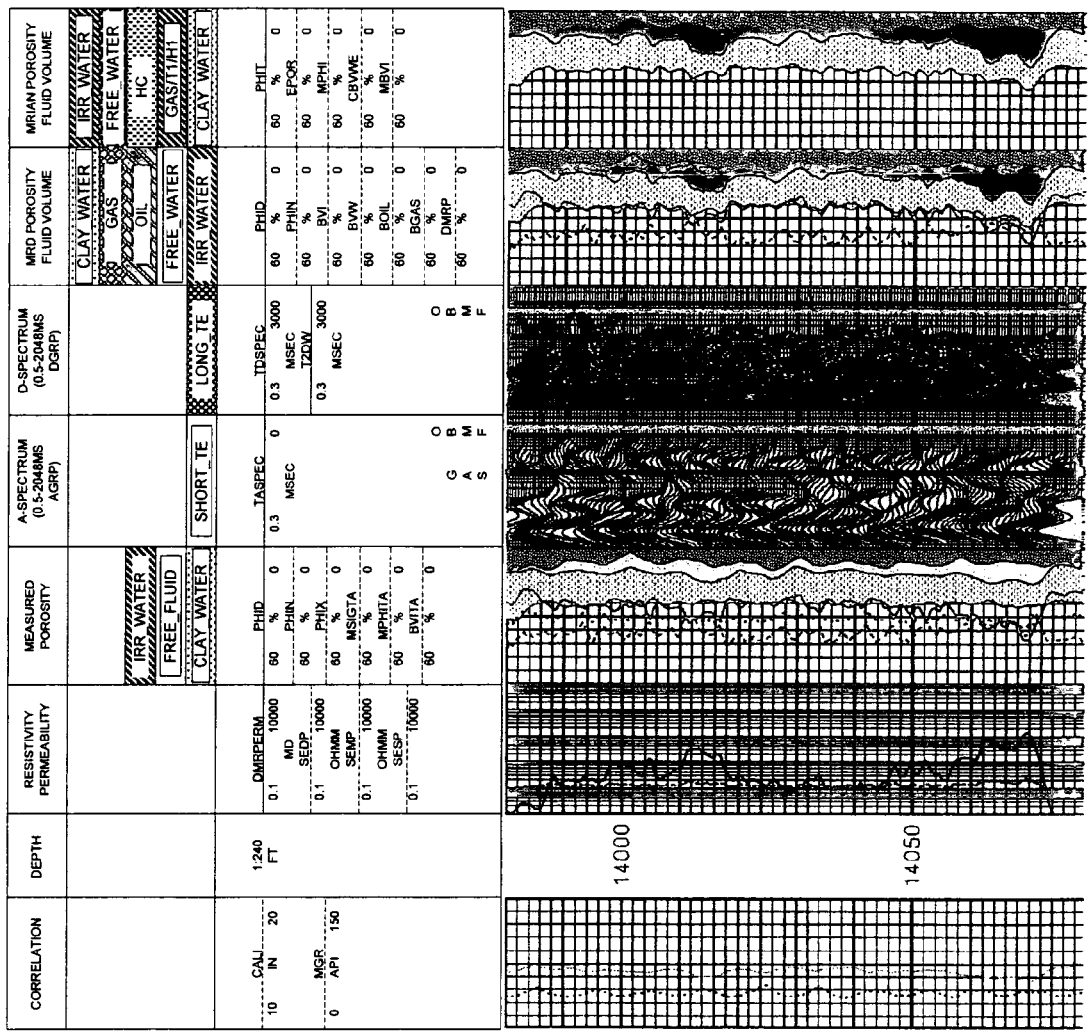
FIG. 6 illustrates shows log data similar to that in FIG. 5, but from a known, poor quality gas sand in which the identified hydrocarbons primarily comprise gas.

FIG. 6 shows log data from known, poor quality gas sand. The conventional nuclear porosity logs provide no definitive indication of gas and the recorded MRIL® log (Track III) shows approximately 6 p.u. of free fluid through the zone on average. As shown in FIG. 4, the new methods described herein clearly identify this zone as gas bearing. The unambiguous identification of this gas zone is a good indication the new method has good sensitivity to relatively small volumes of gas.

Figure 7:
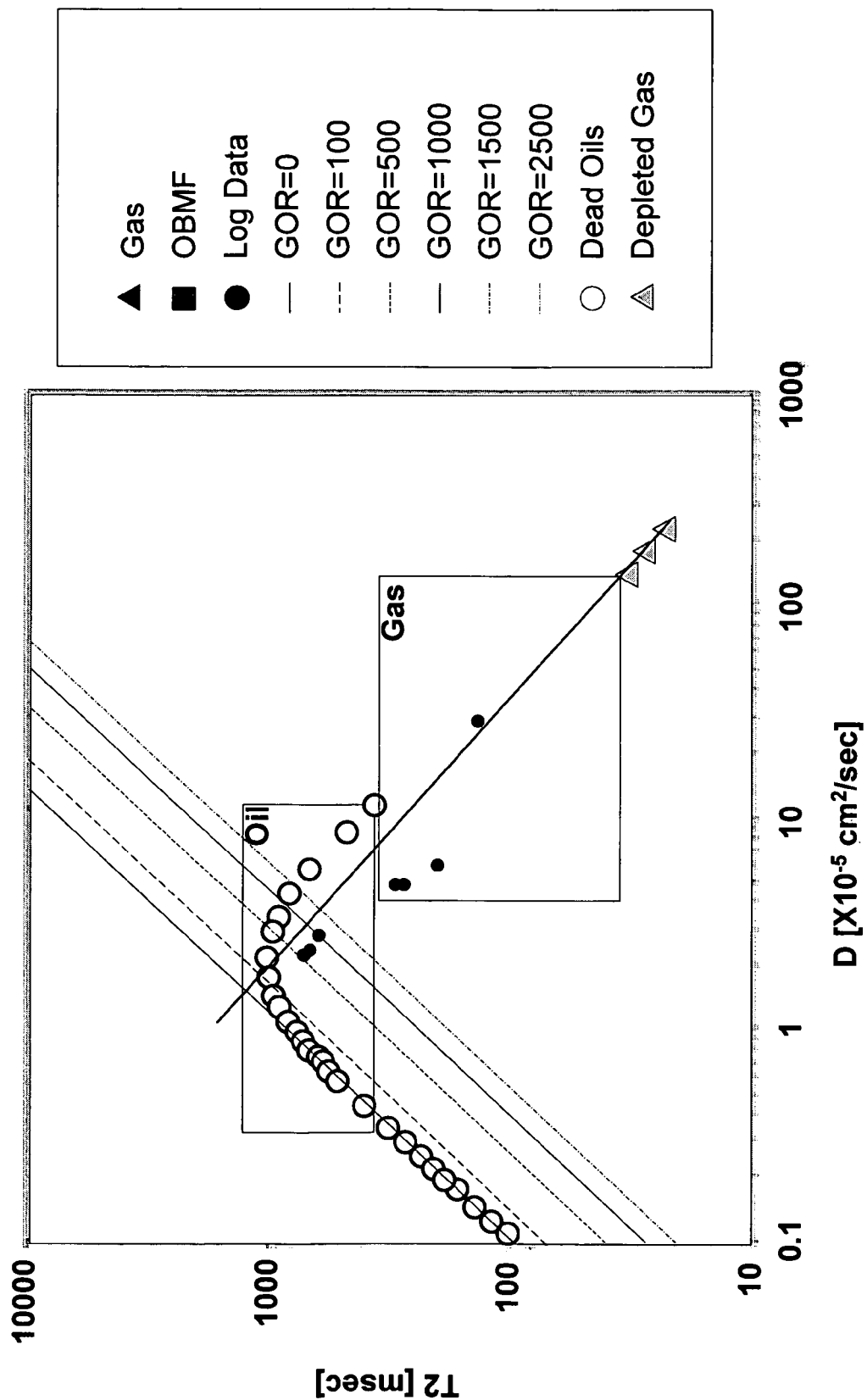
FIG. 7 shows, in a crossplot plot similar to that shown in FIG. 4, based on data from an oil-mud drilled well in Equatorial Guinea, a distinct separation among oil and gas responses. In addition, it suggests, as does FIG. 4, that points falling in the neighborhood of the pure methane response and to the lower right (predicted to be depleted gas volume) likely indicate miscible mixing of pressure depleted gas and oil-based mud filtrates.

The data presented in FIG. 7 are from an oil-mud drilled well in Equatorial Guinea. In this example, there is a distinct separation among oil and gas responses. The gas points in this example also show a significant hydrogen index effect on the MRIL® porosity compared to conventional neutron density cross plot porosity. Similarly, a significant hydrogen index effect on the MRIL® porosity is not observed for the oil points in this example.

Although the invention has been described in detail, it admits of various variations as would be obvious to one of ordinary skill in the art. Accordingly, the invention is to be interpreted in accordance with the following claims rather than by interpreting the illustrative embodiments described above as a limitation on the scope of the invention.

What is claimed is:

1. A method for estimating the type of hydrocarbons in a formation surrounding a borehole drilled with an oil-based mud, comprising:
   (a) providing a mathematical model for a fluid mixture of native hydrocarbons and oil-based mud in the formation;
   (b) providing NMR signals from one or more locations in the formation; and
   (c) estimating the type of native hydrocarbons in said one or more locations in the formation based on the provided mathematical model and the provided NMR signals;
   wherein the mathematical model is based on T2 relaxation and effective diffusion D, and the step of estimating comprises generating, based on the NMR signals, an apparent T2 decay time and an effective diffusion constant to construct a T2-diffusion constant crossplot; and comparing the mathematical model with the constructed crossplot.

2. The method of claim 1, further comprising the step of detecting presence of native oil if presence of gas or a mixture of gas and oil-based mud filtrate does not account for substantially all of the NMR signals.

3. The method of claim 1, wherein a known diffusion constant for at least one oil used in the oil-based mud allows estimation of the oil-based mud contributions to the $T^2$-diffusion constant crossplot.

4. The method of claim 1, further comprising the step of distinguishing native oils from the oil-based mud in at least one of said one or more locations in the formation.

5. The method of claim 1 further comprising selecting at least one oil with known properties in the oil-based mud in the step of providing the mathematical model.

6. The method of claim 1, wherein step (a) comprises modeling boundaries between native hydrocarbon types and oil-based mud in the mathematical model.

7. The method of claim 6, further comprising the step of providing a resistivity log to assist in modeling boundaries between native hydrocarbon types and oil-based mud.

8. The method of claim 6, wherein the step of modeling boundaries comprises using one or more of: (1) fuzzy logic rules; (2) neural network modeling; and (3) empirical observations.

9. A method for nuclear magnetic resonance (NMR) based estimation of petrophysical properties of an earth formation surrounding a well drilled with oil-based muds, comprising:

generating one or more of differential NMR signals adjusted to reduce contributions from water;

estimating an apparent $T_2$ decay time and an effective diffusion constant from the one or more of the differential NMR signals; and transforming the apparent $T_2$ decay time and effective diffusion constant into an indication of contributions of hydrocarbon types, such as gas mixed with oil-based muds, gas alone, native oils, and native oil mixed with oil-based mud, wherein the step of transforming is performed using one or more of: (1) a known diffusion constant for an oil-based mud; (2) fuzzy logic for assigning NMR signals to one or more by hydrocarbon types; and (3) neural networks for dynamically adjusting the network response to input signals from known hydrocarbon types.

10. The method of claim 9, wherein an array of echo differences is constructed by taking the difference between a long wait time echo train and a short wait time echo train echo by echo.

11. The method of claim 10, wherein the apparent $T_2$ decay time is estimated using a functional model describing signal decay in the array of echo differences.

12. The method of claim 11, wherein the apparent $T_2$ decay time is estimated by using a stretched exponential function:

$$E(t) = A e^{-\left[\frac{t}{T_2}\right]^\alpha}$$

wherein, E(t) represents the differential echo amplitude at echo time, t; A represents an amplitude of a differential signal; and $\alpha$ is the stretch factor.

13. The method of claim 9, wherein the differential NMR signals are generated by the differential spectrum method.

14. The method of claim 13, wherein each of the differential NMR signals is obtained by subtracting a short wait time $T_2$ distribution from a long wait time $T_2$ distribution at corresponding inter-echo times.

15. The method of claim 14, wherein an apparent $T_{2B}$ bulk decay time and the effective diffusion constant is estimated using the expressions:

$$\frac{1}{T_{2S}} = \frac{1}{T_{2B}} + \frac{D(\gamma G c T E_S)^2}{12}, \text{ and } \frac{1}{T_{2L}} = \frac{1}{T_{2B}} + \frac{D(\gamma G c T E_L)^2}{12},$$

wherein $\gamma$ represents a gyromagnetic ratio for hydrogen protons, G is the magnetic field gradient, c is a constant for taking into account combined effects of spin dynamics associated with mixing of direct and simulated echoes in a gradient magnetic field, $T_{2S}$ is a decay time for a short interecho time, $T_{2L}$ is a decay time for a long interecho time, $TE_S$ is a short inter-echo spacing, and $TE_L$ is a long inter-echo spacing.

16. The method of claim 9 further comprising the step of resolving ambiguities between mixture of oil-based mud filtrate and native oils and/or condensate on one hand and water bearing formation invaded with oil-based mud by a deep reading resistivity log on the other hand.

17. The method of claim 9 further comprising confirming detection of a native hydrocarbon with the aid of one or more of a porosity and a resitivity log.

18. A method for obtaining an estimate, based on NMR signals, of hydrocarbons in a formation surrounding a borehole drilled with the aid of oil-based mud, comprising:

constructing an array of echo differences by taking the echo-by-echo difference between a long wait time and a short wait time echo trains;

estimating an apparent $T_2$ decay time in the array of echo differences; and estimating native hydrocarbon contributions to the apparent $T_2$ decay time to obtain an indication of native oil type, based at least in part on a failure of a gas contribution to substantially account for the estimated apparent $T_2$ decay time.

19. The method of claim 18, wherein the indication of the native oil type is confirmed with the aid of one or more of a porosity and a resitivity log.

20. The method of claim 18, wherein the step of estimating native hydrocarbon contributions comprises constructing an apparent $T_2$ decay time versus effective diffusion constant plot, which distinguishes between native hydrocarbons and the oil-based mud by taking into account a known diffusion constant for an oil used in the oil-based mud.

* * * * *